United States Patent
Cole (10) Patent No.: US 8,253,932 B1
(45) Date of Patent: Aug. 28, 2012

(54) LASER AND CORNER CUBE REFRACTIVE-INDEX STRUCTURE PARAMETER SYSTEM

(75) Inventor: Walter P. Cole, Springfield, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 271 days.

(21) Appl. No.: 12/819,410

(22) Filed: Jun. 21, 2010

(51) Int. Cl.
G01N 21/41 (2006.01)
G01N 21/55 (2006.01)

(52) U.S. Cl. ...................................... 356/128; 356/445

(58) Field of Classification Search ........... 356/128–137
See application file for complete search history.

(56) References Cited

U.S. PATENT DOCUMENTS 4,632,563 A * 12/1986 Lord, III ...................... 356/437
5,532,813 A * 7/1996 Ohishi et al. .................. 356/5.01

OTHER PUBLICATIONS

L.C. Andrews and R.L. Phillips, "Weak and strong fluctuations conditions" in Laser Beam Propagation through Random Media, SPIE Press, Bellingham, WA, pp. 140-141 (2005).
L.C. Andrews and R.L. Phillips, "Extended Huygens-Fresnel Principle" in Laser Beam Propagation through Random Media, SPIE Press, Bellingham, WA, pp. 234-241 (2005).
C. Cooke et al., "Ranging, Communications, and Simulation Systems," in The Infrared Handbook, W.L. Wolfe and G.J. Zissis, eds. (IRIA Ctr, Env. Res. Inst. of MI, Navy) (1985).
O. Steinvall, "Effects of target shape and reflection on laser radar cross sections," Appl. Opt. 39, 4381-4391 (2000).
F. Vetelino et al., "Characterizing the propagation path in moderate to strong optical turbulence," Appl. Opt. 45, 3534-3543 (2006).
W. Cole et al., "Atmospheric-turbulence-effects correction factors for the laser range equation," Opt. Eng. 47(12), 126001-1 (2008).
J. Ricklin et al., "Atmospheric turbulence effects on a partially coherent Gaussian beam: implications for free-space laser communication," J. Opt. Soc. Am. 19, 1794-1802 (2002).
G. Berman et al., "Beam wandering in the atmosphere: the effect of partial coherence," Phys. Rev. E 76, 056606-1 (2007).
I. Toselli et al., "Free-space optical system performance for laser beam propagation through non-Kolmogorov turbulence," Opt. Eng. 47(2), 026003-1 (2008).
G. Berman et al. "Photon distribution function for long-distance propagation of partially coherent beams through the turbulent atmosphere," Phys. Rev. A 74, 013805-1 (2006).
R. Fante, "Electromagnetic Beam Propagation in Turbulent Media," Proceedings of the IEEE, 63 (12), 1669-1692 (1975).

(Continued)

*Primary Examiner* — Michael P Stafira
(74) *Attorney, Agent, or Firm* — Henry S. Goldfine (57) ABSTRACT

A near-IR laser laser-and-corner cube system for determining the refractive-index structure parameter by providing the return power of the retroreflected laser beam from the corner cube, which return power correlates to the refractive-index structure parameter. The system is economical, physically containing only (1) the laser which emits a near-IR wavelength output beam, (2) a 50/50 splitter, to receive back the retroreflected return beam from the corner cube along the same optical axis as the output beam, in a monostatic configuration; (3) the target corner cube; (4) a receiving focus lens; (5) a spectral filter and (6) a power meter to provide the monostatic measurement of the return power. Critically the ratio of the area of the corner cube to that of the receiving focus lens is at least 1:2, to obtain meaningful power measurements—to correlate to pre-calculated refractive-index structure parameters.

8 Claims, 5 Drawing Sheets

OTHER PUBLICATIONS

S. Bendersky et al., "Atmospheric optical turbulence over land in middle east coastal environments: prediction modeling and measurements," App. Opt. 43(20), 4070-4079 (2004).

A. MacDonald et al., "Maximum a posteriori image and seeing condition estimation from partially coherent two-dimensional light . . . ," Opt. Eng. 45(8), 086201-1 (2006).

J. Strohbehn, "Line-of-sight wave propagation through the turbulent atmosphere," Proceedings of the IEEE, 56(8), 1301-1318 (1968).

D. Hutt, "Modeling and measurements of atmospheric optical turbulence over land," Opt. Eng. 38(8), 1288-1295 (1999).

G. Gimmestad et al., "Laser remote sensing of atmospheric turbulence", Proceedings of the SPIE, 5087, 167-172 (2003).

Y. Jiang et al., "Measurement of optical intensity fluctuation over an 11.8 km tubulent path," Optics Express, 16(10), 6963-6973 (2008).

N. Sugimoto, "Video camera measurements of amospheric turbulence using the telescope imiage of a distant light source," Appl. Opt. 30(4), 365-367 (1991).

S. Zamek et al., "Turbulence strength estimation from an arbitrary set of atmospherically degraded images," J. Opt. Soc. Am. 23(12), 3106-3113 (2006).

M. Wesely et al., "Atmospheric turbulence parameters from visual resolution," Appl. Opt. 14(4), 847-853 (1975).

M. Vilcheck et al., "Multiple methods for measuring atmospheric turbulence," Proceedings of SPIE 4821, 300-309 (2002).

F. Vetelino et al., "Inferring path average C2/n. values in the marine environment," J. Opt. Soc. Am. 24 (10), 3198-3206 (2007).

* cited by examiner

Fig. 1

500 meters
Figure 2

773 meters
Figure 3

Figure 4

5000 meters
Figure 5

LASER AND CORNER CUBE REFRACTIVE-INDEX STRUCTURE PARAMETER SYSTEM

FEDERAL RESEARCH STATEMENT

The inventions described herein may be manufactured, used and licensed by, or for the U.S. Government, for U.S. Government purposes.

BACKGROUND OF INVENTION

1. Field of the Invention

The present invention relates to a method for determining optical turbulence, as measured by the refractive-index structure parameter, of the atmosphere along a beam propagation path using a simple laser and corner cube system and more particularly such a system involving a particularly sized receiver and corner cube combination.

2. Related Art

A laser beam propagating through the atmosphere encounters random refractive-index fluctuations. These random fluctuations are often referred to as optical or atmospheric turbulence. Such turbulence in the surface layer of the atmosphere, extending upward from the ground to a few tens of meters, is unstable if heat is rising from the ground, as is common during sunshine where the rising heat adds to the turbulence. The surface layer is more stable if the ground is cooler than the air, so that heat is transferred downward, as is common at night and such stability tends to damp turbulence. The surface layer is near neutral if wind shear alone produces almost all of the turbulence, whereas the heat transfer between ground and air is not effective in producing or damping turbulence—which condition typically occurs when the wind is strong and/or solar radiation is weak.

Optical or atmospheric turbulence cause scintillation or twinkling of distant light sources. The strength of this turbulence that produces scintillation is represented by the refractive-index structure parameter, which is denoted by $C_n^2$. In particular, this parameter, $C_n^2$ reflects the optical turbulence impacting a laser beam's characteristics as it is transmitted through a particular region. As a result, measurement of atmospheric parameters to describe the optical turbulence to which a laser beam is subjected as it propagates during field experiments is critical for understanding and predicting the atmospheric effects on the optical wave.

A variety of in situ techniques are known for measuring atmospheric fluxes, including using a sonic anemometer or performing indirect-dissipation measurements using a fine wire thermometer and hot-film anemometers. These prior art methods, however, require excessive capture, processing, and analysis of high data rates. Also, the instruments are not particularly rugged. For example, fine-wire thermometers are subject to hygroscopic-particle contamination. And, finally, such in situ measurement of fluxes at a single point yields point measurements of fluxes which are extremely location dependent. Movement from one location to another produces different readings. To obtain more general readings, for example as part of an ecological or air quality study, it is required to take measurements at a large number of points and to average the resultant data, making the overall collection of data rather cumbersome.

To overcome such prior art problems, U.S. Pat. No. 5,150,171 discloses a method of deriving the refractive-index structure parameter using a scintillometer, which includes a laser light source and a detector aligned to receive light from the laser light source through the atmosphere. A source of incoherent light is aligned with a second detector. One detector circuit measures fluctuations in intensity of the light received from the laser light source; while, a second detector circuit measures fluctuations in intensity of the received incoherent light. The inner scale of turbulence is obtained from a ratio of the two measured variances. With the known inner scale of turbulence, the system utilizes a processor to derive the refractive-index structure parameter from the measured variances of intensity.

While the scintillometer of U.S. Pat. No. 5,150,171 does overcome some of the problems of the prior art, it is complex and necessitates the use of expensive equipment; such that there is a need in the art for a simpler and more cost effective means of measuring $C_n^2$.

SUMMARY OF INVENTION

As a laser beam propagates the path from the transmitter to the target and back to the receiver, the beam encounters random fluctuations in the refractive index of the atmosphere, due primarily to temperature differences, as discussed above. Such refractive index fluctuations distort the beam's wavefront, resulting in a number of effects including spreading of the beam beyond that which occurs in free-space propagation, beam wander, and irradiance fluctuations due to random redistribution of energy in the beam. The beam spreading and irradiance fluctuations typically reduce the energy that is incident on the target and subsequently returned to the receiving aperture. As a result, atmospheric turbulence is a key consideration in returned power predictions.

The distortion of the beam is, as stated, dependent upon the strength of the atmospheric turbulence and is a function of wavelength. The Rytov variance ($\sigma_R^2$) is a known measure used to define the strength of atmospheric turbulence (see, F. S. Vetelino, et al., "Characterizing the propagation path in moderate to strong turbulence," Appl. Opt. 45, 3534-3543 (2006)). The Rytov variance is:

$$\sigma_R^2 = 1.23\, C_n^2 k^{7/6} z^{11/6} \qquad (1)$$

where $C_n^2$ is the refractive-index structure parameter and z is the total propagation distance. For spherical and plane waves, the weak function regime is classified by $\sigma_R^2$ much less than 1, moderate by $\sigma_R^2$ approximately 1, and strong by $\sigma_R^2$ much greater than 1. Further, for a Gaussian-beam wave, the weak regime has the added condition for $\sigma_R^{5/6} < 1$, where $\hat{} = 2z/kW^2$ and is evaluated at the receiver (see, L. C. Andrews and R. L. Phillips, "Weak and strong fluctuations conditions" in Laser Beam Propagation through Random Media, SPIE Press, Bellingham, Wash., pp. 140-141 (2005).

Based upon the extended Huygens-Fresnel equation (see, L. C. Andrews and R. L. Phillips, "Extended Huygens-Fresnel Principle" in Laser Beam Propagation through Random Media, SPIE Press, Bellingham, Wash., pp. 234-241 (2005), as shown in the paper "Atmospheric-turbulence-effects correction factors for laser range equation", by W. P. Cole, et. al., Opt. Eng. 47(12), pp. 126001-4 to 126001-5, (December 2008), incorporated herein by reference, where the beam propagation distance is much less than the propagation distance which the transverse coherent radium of the beam is on the order of the inner scale, the mean irradiance for strong fluctuation conditions can be approximated by a Gaussian function with an effective beam spread in the form of a long-term beam radius ($W_{LT}$), where:

$$W_{LT} \approx W \cdot (1 + 1.63 \cdot \sigma_R^{12/5} \cdot \hat{})^{0.5} \qquad (2)$$

The use of such a long-term beam radius in these calculations is necessary for useful return power predictions due to the significant uncertainty associated with an individual return-power measurement.

As detailed in W. P. Cole, et. al., Opt. Engrg. 47(12), page 126001-5, a corrective term that accounts for differences in receiving power due to beam spread on a circular optic and receiver combination is:

$$T_{turb}=[1-\exp(-2r_{rec}^2/W_{LT}^2)]/[1-\exp(-2r_{rec}^2/W_{rec}^2)] \quad (3)$$

where $r_{rec}$ is the radius of the receiving aperture and $W_{LT}$ is evaluated at z=2R.

For a retroreflective circular optic, the beam radius of the retroreflected beam at the receiver, $W_{rec}$, is obtained by using the first minimum of the beam's Airy diffraction pattern, which accounts for 84% of the total energy of the beam. With this definition for the beam spot radius, the beam radius at the receiver for small angles is:

$$W_{rec} \approx 1.22R\lambda/D_{tar} \quad (4)$$

where $D_{tar}$ is the diameter of the target aperture and $\lambda$ is the wavelength of the beam.

The present invention determines the path-averaged refractive-index structure parameter, $C_n^2$, of the atmosphere along a laser's path through the atmosphere by measuring the full power returned, $P_r$, to a receiving aperture using a laser-and-corner-cube system, where the laser beam is propagated to and from a target and, the current invention measures the return power of the laser beam to determine the $C_n^2$. The relationship between full power returned and $C_n^2$ is not straightforward—but has been determined by the correlation of predicted return power in the absence of optical turbulence, $P_r$, against that of the expected return power at various $C_n^2$.

Experimental results of use of the present invention provide a surprisingly good correlation to the theoretic determination of return power, which is calculated by the a general form of the laser range equation, derived from basic geometric principles, with the addition of a turbulence correction factor, $T_{turb}$, detailed below, (see C. Cooke, J. Cernius, and A. J. LaRocca, "Ranging, Communications, and Simulation Systems," in The Infrared Handbook, W. L. Wolfe and G. J. Zissis, eds. (IRIA Center, Environmental Research Institute of Michigan, for the Office of Naval Research, Dept. of the Navy, 1985), Chap. 23, p 23-6; and also see, O. Steinvall, "Effects of target shape and reflection on laser radar cross sections," Appl. Opt. 39, 4381-4391 (2000)—documents which are incorporated herein by reference):

$$P_r=((P_{laser}P_{shape}D_{rec}^2)/\theta_T^2R^4)\cdot\sigma_{tar}\cdot T_a^2\cdot T_T T_{rec}\cdot T_{turb} \quad (5)$$

Where $P_r$ is the return power; $P_{laser}$ is the power of the laser; $P_{shape}$ is a factor to account for the differences between the transmitted beam shape's irradiance profile and an equivalent beam with a uniform irradiance (for a typical laser operating in the lowest-order Gaussian mode, $P_{shape}$=2); $D_{rec}$ is the diameter of the receiver; $\theta_T$ is 1.7 milli-radians, which is the divergence angle for particularly preferred near IR lasers applicable for the present invention; R is the laser-transmitter-to-target range, i.e. distance (which can vary from about 300 to about 5000 meters, preferably about 500 to about 2000 meters); $\sigma_{tar}$ is the optical cross section of the target; $T_a$ is the atmospheric transmission at a particular wavelength (which if perfect is 1, but, is in fact always less than 1, and in the case of the particular preferred laser wavelengths, such as 1064 nm, is about 0.975); $T_T$ is a transmitter factor, which accounts for the optics effects between the laser and target retransmission (in the present systems, this factor is approximately 1); $T_{rec}$ is a transmission factor, which accounts for the return beam from the receiver (once again, in the present systems, this factor is approximately 1); and $T_{turb}$ is a corrective term that accounts for differences in receiving power due to beam spread on a circular optic receiver (as discussed above).

The present invention is embodied within a laser-and-corner cube system, which system includes, preferably a near-IR laser having high transmission through the atmosphere, which laser has a $TEM_{00}$ mode to maximize the uniformity of the laser's impact on the target and thereby maximizes return power; a 90/10 beam splitter can be provided as a means to monitor the output beam; a 50/50 beam splitter provides a means to emit a 50% output laser beam toward the target (the other 50% going to a beam dump) and also to allow for monostatic measurement of the return power; and, a target corner cube accepts the output beam and provide a retroreflected return beam with known diffraction characteristics. The retroreflected return beam hits the 50/50 beam splitter, whereupon half is again dumped to the beam dump, and the other half, the half of interest for measuring the return power from the target corner cube, is channeled through a receiving or focus lens, to a spectral filter and return power meter. So, a particular embodiment would be such that, for example, a 400 W $TEM_{00}$ laser output beam would initially impact the 90/10 splitter, 10% or 40 W being diverted to a focusing lens and output power monitoring meter; the balanced, 90% or 360 W, is directed to the 50/50 beam splitter, where 180 W would be directed to a beam dump and 180 W exit the laser to impact and be retroreflected by the target corner cube, as a return beam. The retroreflected return beam (now less that 180 W) would impact the 50/50 splitter, again 50% (now less than 90 W) going to a beam dump and 50% going to a receiving or focus lens, then to a spectral filter and the return power meter. Surprisingly, it has been found that the area of the corner cube in relation to the receiving or focus lens is critical. As detailed below, experiments where the area of the corner cube to the receiving lens was in the order of 2:1, respectively, resulted in a flat return power profile in relation to $C_n^2$, such that for half of the power levels of interest, it was impossible to establish the $C_n^2$. However, where the area of the corner cube to the receiving lens was at least 1:2, and preferably 1:3, and most preferably in the order of 1:5 or more, the slope of the return power to $C_n^2$ profile had sufficient slope to easily distinguish changes of $C_n^2$ with changes of return power.

In alternative embodiments, to control the transmission beams properties, a half-wave plate followed by a polarizing beam splitter can be used as a variable attenuator, which combination is often used in optical systems. Also, an exit mirror can be used to guide the beam to the corner cube target and an entrance mirror can be used to guide the return beam to the spectral filter and return beam power meter.

The transmission beams characteristics for a typical 500 meter propagation path include a power variable from 38 to 62 mW, a spot size at the transmitter of 5.5 mm, and a measured divergence angle ($\theta_T$) of $1.45 \times 10^{-3}$ rad. In order to measure the return beam power, the receiving optics included the beam splitter, mentioned above, that intercepted the retroreflected return beam, a focusing lens, and a narrowband spectral filter. To prevent distortion of the beam profile, the various lens should be of optical quality glass—with surface flatness of $\lambda/10$ ($\lambda$=633 nm) and scratch-dig of 40-20 or better.

Further features and advantages of the present invention will be set forth in, or apparent from, the detailed description of preferred embodiments thereof which follows.

DETAILED DESCRIPTION

Figure 1:
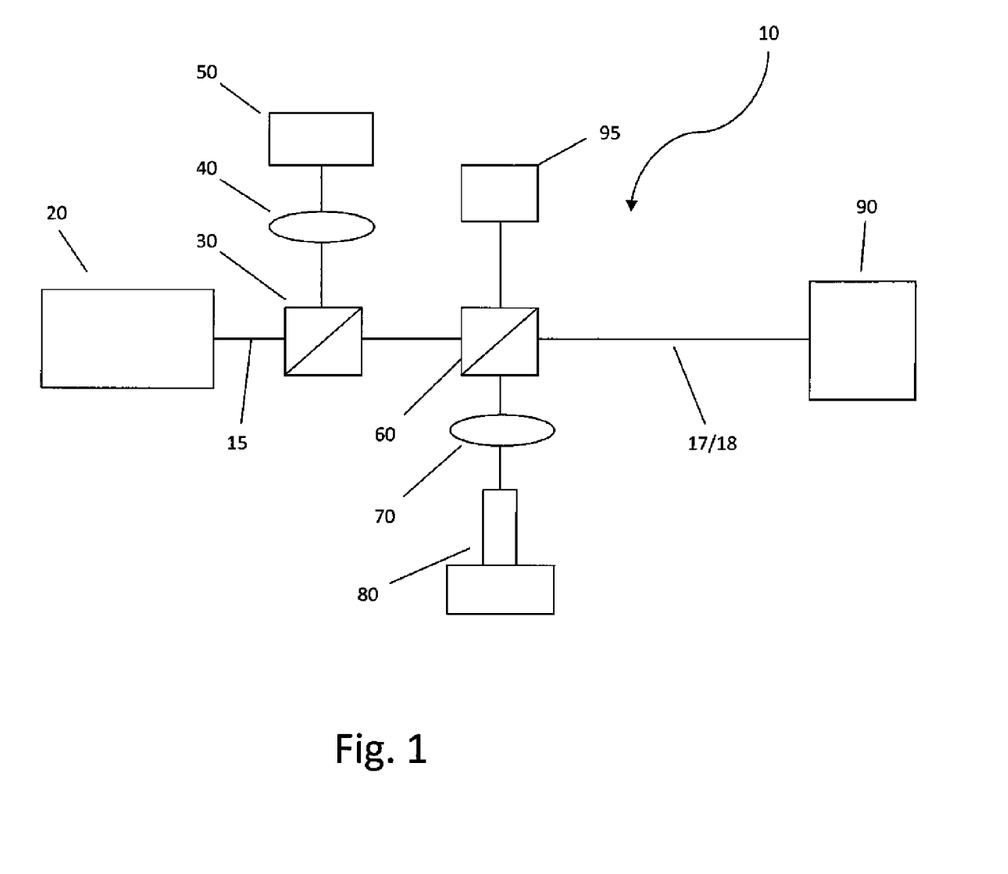
FIG. 1 is a schematic, not to scale, of the preferred embodiment of the present invention.
Figure 2:
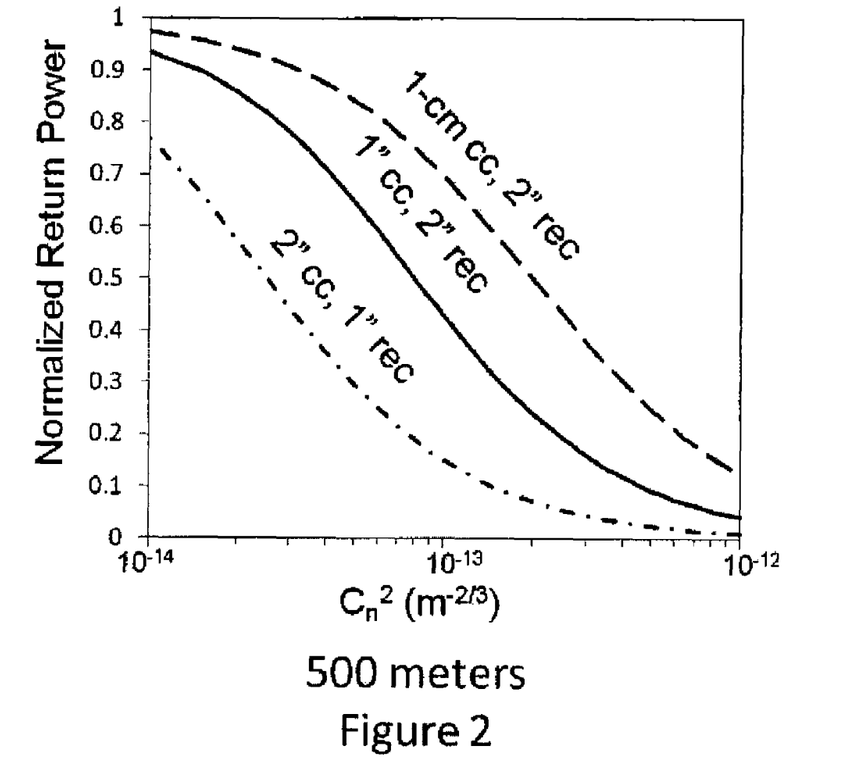
FIG. 2 is a normalized return power function of $C_n^2$ for three different sets of corner-cube (cc) and receiver (rec) diameter sizes of the present invention, wherein the range to target is approximately 500 meters.
Figure 3:
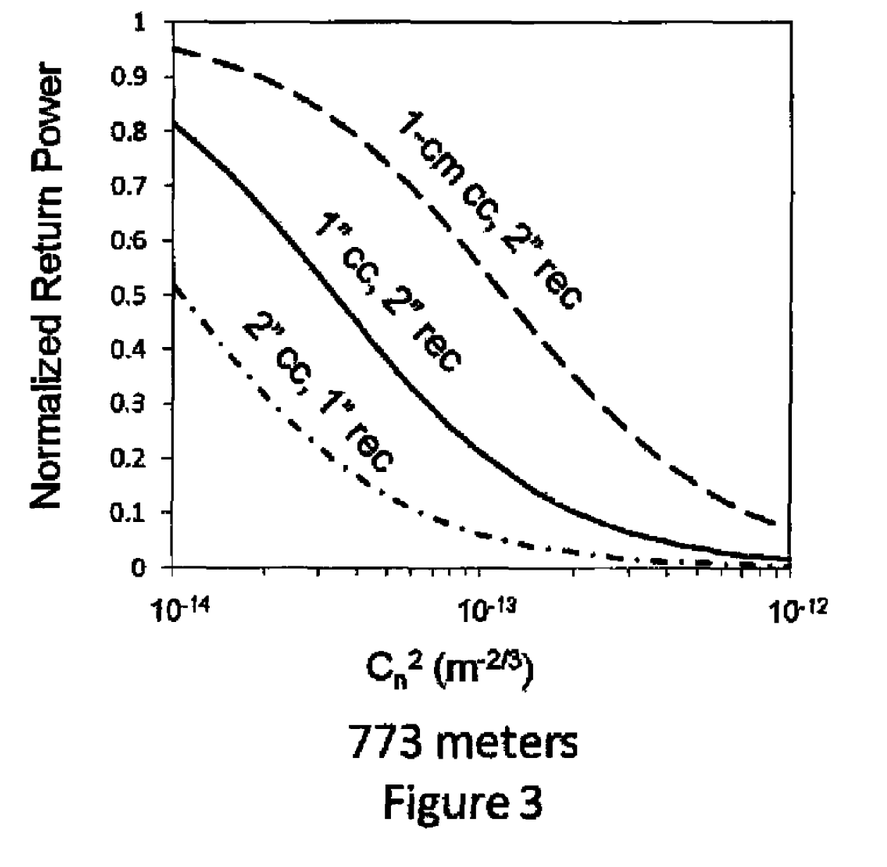
FIG. 3 is a normalized return power function of $C_n^2$ for three different sets of corner-cube (cc) and receiver (rec) diameter sizes of the present invention, wherein the range to target is approximately 773 meters.
Figure 4:
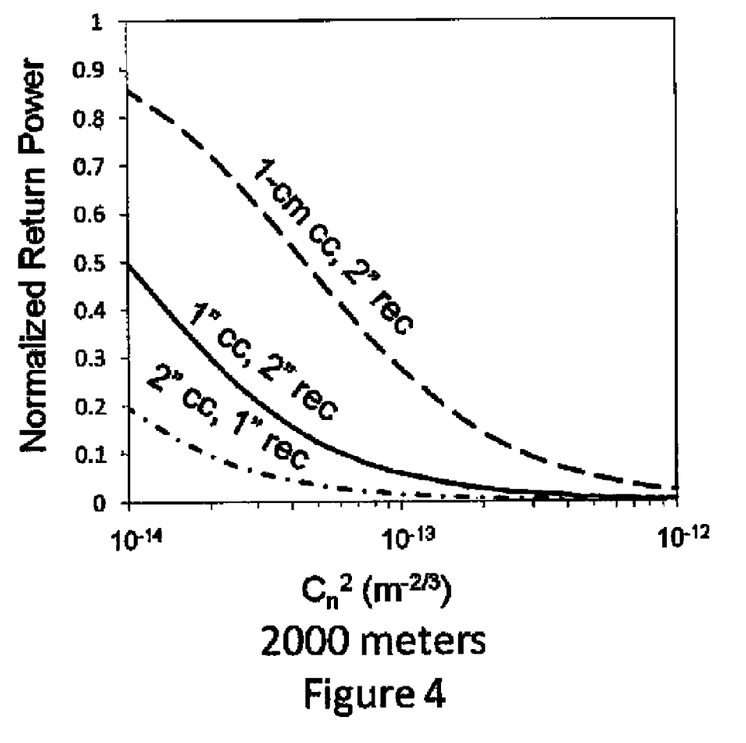
FIG. 4 is a normalized return power function of $C_n^2$ for three different sets of corner-cube (cc) and receiver (rec) diameter sizes of the present invention, wherein the range to target is approximately 2000 meters.

Referring to FIG. 1, a preferred embodiment of the subject invention includes a laser-and-corner cube system, 10, wherein the laser, 20, is a $TEM_{00}$ laser which emits a spatial profile beam, 17, that is very nearly Gaussian (greater than 95%) and that does not change as it propagates, i.e. from when it emerges from the laser right into the far field. Such $TEM_{00}$ laser beams can be generated by Nd:YAG lasers available from Litron Lasers NA, in Bozeman Mont., or CrystaLaser diode-pumped solid state continuous wave lasers, available from CrystaLaser, in Reno, Nev. The most preferred laser, 20, for measurements at ranges of approximately 500 meters is such a continuous laser with a power variable from 38 to 62 mW, a spot size at the transmitter of 5.5 mm, and a measured divergence angle ($\theta_T$) of $1.45 \times 10^{-3}$ rad, the wavelength should preferably be near IR, with a particularly preferred wavelength of 1064 nm.

Continuing to refer to FIG. 1, preferably a 90/10 beam splitter, 30, is located so as to divert 10% of the laser beam, 15, to a focusing lens, 40, and output power meter, 50, thereby providing a means of monitoring the output of the laser, 20. A 50-50 beam splitter, 60, is positioned to emit 50% of the laser beam incident thereon from the laser toward a target, and to allow for monostatic measurement of the return power (note: the unused portion of the laser beam is channeled to a beam dump, 95). The target is a corner cube, 90, which is positioned to accept the output beam, 17, and provide a retroreflected return beam, 18, with a known diffraction pattern; which retroreflected return beam, 18, is returned to the 50-50 beam splitter, which channels the return beam through a second set of focus lens (i.e. the receiving lens), 18, to a spectral filter and return power meter, 80. The spectral filter provides necessary noise reduction, i.e. a narrow band spectral filter of other than the particular wave length of interest emitted by the laser. A particularly preferred spectral filter is available from Thorlabs, Inc, Newton, N.J., which has a center wavelength of 1064 nm+/-2—the most preferred laser beam wavelength.

As initially discussed above, it has been found that the area of the corner cube, 90, in relation to the receiving lens, 70, is critical. As detailed herein, experiments where the area of the corner cube, 90, to the receiving lens, 70, was in the order of 2:1, respectively, resulted in a flat return power profile in relation to $C_n^2$, such that for half of the power levels of interest, it was impractical to establish the $C_n^2$. However, where the area of the corner cube, 90, to the receiving lens, 70, was in the order of 1:2 to 1:5 or more, the slope of the return power to $C_n^2$ profile had sufficient slope to easily distinguish changes of $C_n^2$ with changes of return power. A particularly preferred corner cube, 90, to receiving lens, 70, relationship is a 1-cm corner cube and a 2 inch receiving lens. In such a most preferred embodiment, with the receiving elements consisting of a 2 inch (5 cm) diameter receiving lens, 70, a Coherent LM2-Vis, silicon optical sensor (RoHS), power head with a spectral filter combination can be used, available from Coherent Inc, of Santa Clara, Calif.

Using the $P_r$ model developed above, a series of experimental measurements were made and the $C_n^2$ values were obtained over a range of interest $10^{-14}$ to $10^{-12}$ $m^{-2/3}$. The measurements were made using the preferred 1064 nm $TEM_{00}$ laser with various size corner cube and receiver area sizes. For example, a particular $P_r$ was measured and $C_n^2$ was calculated as follows and then verified against a measurement using a Scintec model BLS900 Large Aperture Scintillometer, Scintec Corporation, Atlanta/Alpharetta, Ga.: Given/known values: $P_{laser}=0.277$ W; $P_{shape}=2$ (beam shape factor for a uniform beam); $D_{rec}=0.0508$ m; $A_{rec}=T_T \cdot D_{rec}^2/4 \cdot \cos(\pi/4)$ (effective receiver aperature); $\sigma_{tar}=134,606 \cdot m^2/sr$ (SLCT measurement); $T_a=0.97$ (HELEEOS estimate for particular testing conditions); $\theta_T=1.7 \times 10^{-3}$ rad; $D_{tar}=0.0254$ m; R=773 m; $T_T=0.95$ (effective laser power measured after beam splitter); $T_{rec}=(0.68)(0.984)(0.7)(0.95)=0.445$ (considering beam splitter, focusing lens, and spectral filter transmissions, and the reflectivity of the entrance mirror, respectively); and $\lambda=1064 \times 10^{-9}$ m.

Calculation of $P_r$: Providing a series of $C_n^2$ values—such as $C_n^2=7.74 \times 10^{-14}$ $m^{-2/3}$, the following calculation was made:

$$W_{rec}=(1.22)R\lambda/D_{tar};$$

$\hat{ } = 2z/kw_{rec}^2$ (where z=(2)(773)=1546 m, the total beam propagation distance);

$\sigma_R=(1.23 \ C_n^2 \cdot k^{7/6} \cdot z^{11/6})^{0.5}$ (again use the total propagation distance);

$W_{LT}=W_{rec} \cdot (1+1.63 \cdot \sigma_R^{12/5} \cdot \hat{\ })^{0.5}$;

$R_{rec}=0.0254$ m;

$T_{turb}=[1-\exp(-2r_{rec}^2/W_{LT}^2)]/[1-\exp(-2r_{rec}^2/W_{rec}^2)]=0.268$; and $P_r=((P_{laser}P_{shape}D_{rec}^2) \cdot \sigma_{tar} \cdot T_a^2 \cdot T_T \cdot T_{rec} \cdot T_{turb} \approx 14.1$ µW Result: the calculation of $P_r$ was confirmed by the scintillometer measurement of $C_n^2=7.74 \times 10^{-14}$ $M^{-2/3}$ and 14.3 pW.

Figure 5:
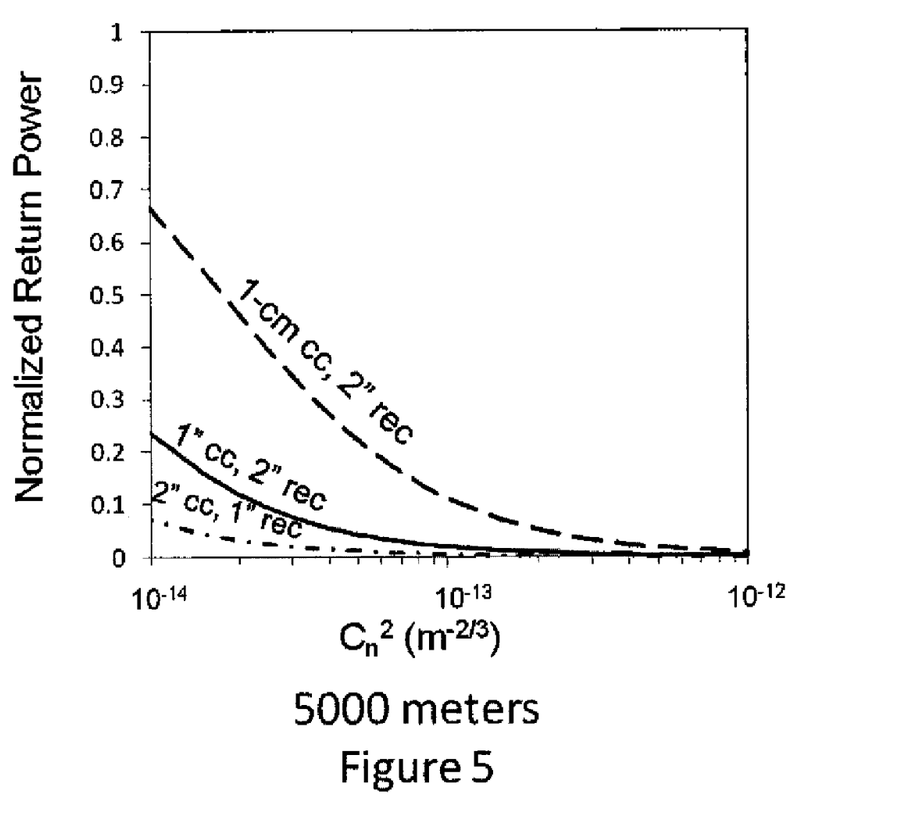
FIG. 5 is a normalized return power function of $C_n^2$ for three different sets of corner-cube (cc) and receiver (rec) diameter sizes of the present invention, wherein the range to target is approximately 5000 meters.

The series of experiments or examination of results from the model, using laser-and-corner-cube systems of the present invention, mentioned above provided the results shown in the graphs of FIGS. 2, 3, 4 and 5—the results of which were verified as being accurate for the experiments using the Scintec model BLS900 Large Aperture Scintillometer. Measurements were made at a propagation distances, i.e. spacing between the laser and target corner cube, of respectively, 500 meters (FIG. 2); 773 meters (FIG. 3); while examination of results using the model were conducted at 2000 meters (FIG. 4); and 5000 meters (FIG. 5). The measurements were all made under comparable ambient conditions and at each distance using three particular corner cube to receiver proportionality areas—i.e. (i) a 2 inch corner cube to a 1 inch receiver (2:1); (ii) a 1 inch corner cube to a 2 inch receiver (1:2); and (iii) a 1 cm corner cube to a 2 inch receiver (1:5). As clearly shown in FIG. 2, the slope of the 1:1 corner cube to receiver area is such that there is little sensitivity to distinguish $C_n^2$ over the upper half of the desired $C_n^2$ range, $10^{-13}$ to $10^{-12}$, which is not the case for the either the 1:2 or 1:5 relative corner cube to receiver area combinations. This lack of sensitivity and $C_n^2$ measurement ability becomes significantly worse as the propagation distance increase—such that in the case of either the 2000 or 5000 m measurements, it is impossible to use the 2:1 corner cube to receive area combination for any $C_n^2$ measurement over the entire $10^{-14}$ to $10^{-12}$ $C_n^2$ range of interest.

It is clear to anyone of ordinary skill in the art, that a complete series of graphs similar to FIGS. 2 to 5 can be calculated and verified, such that by simply comparing the return power at any given distance of propagation, the $C_n^2$ corresponding $C_n^2$ value could be obtained. Alternately, it would be well within the skill of anyone of ordinary skill in the art, to simply interface the output of the receiver spectral filter/power meter to a general purpose computer, to calculate the $C_n^2$ from the return power.

Although the invention has been described above in relation to preferred embodiments thereof, it will be understood by those skilled in the art that variations and modifications can be effected in these preferred embodiments without departing from the scope and spirit of the invention.

What is claimed is:

1. A laser and corner cube system for determining the refractive-index structure parameter, the system comprising:
    a laser which emits a near-IR wavelength output beam, a 50/50 splitter, and a return meter subsystem;
    a target corner cube, which is located a distance of from about 300 to about 5000 meters from the laser;
    the near IR wavelength beam is directed to the 50/50 splitter, where 50% is directed to a beam dump, and the balance of the near-IR wavelength beam is directed to the target corner cube, such that the retroreflected return beam from the corner cube will be received along the same optical axis in a monostatic configuration;
    the return beam will impact the 50/50 splitter, which redirects 50% thereof through a receiving focusing lens, to a spectral filter, and then to a power meter resulting in monostatic measurement of the return power;
    wherein, the ratio of the area of the corner cube to that of the receiving focus lens is at least 1:2; and
    means to correlate the return power measurement to obtain the refractive-index structure parameter.

2. The laser and corner cube system for determining the refractive-index structure parameter of claim 1, wherein the laser emits a $TEM_{00}$ beam.

3. The laser and corner cube system for determining the refractive-index structure parameter of claim 1, wherein the near-IR wavelength output beam initially Is directed to a 90/10 splitter, such that 10% of the output beam, an output measurement beam, is directed to an output power meter subsystem, which comprises a first focusing lens and to an output meter in order to monitor the true output power of the system; and such that the 90% balance of the output beam is directed to the 50/50 splitter.

4. The laser and corner cube system for determining the refractive-index structure parameter of claim 1, wherein the wherein, the ratio of the area of the corner cube to that of the receiving focus lens is at least 1:3.

5. The laser and corner cube system for determining the refractive-index structure parameter of claim 1, wherein the wherein, the ratio of the area of the corner cube to that of the receiving focus lens is in the order of 1:5 or more.

6. The laser and corner cube system for determining the refractive-index structure parameter of claim 1, wherein the near-IR wavelength output beam initially Is directed to a half-wave plate and wherein the 50/50 splitter is a polarizing beam splitter.

7. The laser and corner cube system for determining the refractive-index structure parameter of claim 1, wherein the means to correlate the return power measurement to obtain the refractive-index structure parameter is to compare the return power measurement to a pre-calculated graph relating return power measurement to refractive-index structure parameter for the particular distance between the laser and corner cube.

8. The laser and corner cube system for determining the refractive-index structure parameter of claim 1, wherein the means to correlate the return power measurement to obtain the refractive-index structure parameter is to input the return power measurement into a general purpose computer, which computer then calculates the refractive-index structure parameter given the distance between the laser and the refractive-index.

* * * * *